United States Patent
Sogard et al.

(10) Patent No.: US 7,837,619 B2
(45) Date of Patent: Nov. 23, 2010

(54) TRANSEPTAL APPARATUS, SYSTEM, AND METHOD

(75) Inventors: David J. Sogard, Edina, MN (US); Leonard B. Richardson, Brooklyn Park, MN (US); Kent D. Harrison, Maple Grove, MN (US); Diane M. Sheahen, Blaine, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1124 days.

(21) Appl. No.: 11/207,317

(22) Filed: Aug. 19, 2005

(65) Prior Publication Data

US 2007/0043318 A1    Feb. 22, 2007

(51) Int. Cl.
  A61B 1/00   (2006.01)
  A61B 17/08  (2006.01)
(52) U.S. Cl. ...................... 600/139; 606/213
(58) Field of Classification Search ............. 606/127, 606/129, 130, 41, 48, 49, 50, 213; 600/114, 600/139, 146, 153
See application file for complete search history.

(56) References Cited

U.S. PATENT DOCUMENTS

| | | | |
|---|---|---|---|
| 5,370,675 A | 12/1994 | Edwards et al. | |
| 5,749,889 A * | 5/1998 | Bacich et al. | 606/198 |
| 5,769,790 A | 6/1998 | Watkins et al. | |
| 5,919,200 A | 7/1999 | Stambaugh et al. | |
| 5,944,738 A | 8/1999 | Amplatz et al. | |
| 6,007,514 A | 12/1999 | Nita | |
| 6,024,718 A | 2/2000 | Chen et al. | |
| 6,352,503 B1 * | 3/2002 | Matsui et al. | 600/104 |
| 6,378,501 B1 | 4/2002 | Hisato et al. | |
| 6,458,100 B2 | 10/2002 | Roue et al. | |
| 6,482,224 B1 | 11/2002 | Michler et al. | |
| 6,645,225 B1 | 11/2003 | Atkinson | |
| 6,650,923 B1 | 11/2003 | Lesh et al. | |
| 6,716,184 B2 | 4/2004 | Vaezy et al. | |
| 6,755,790 B2 | 6/2004 | Stewart et al. | |
| 6,776,784 B2 | 8/2004 | Ginn | |
| 7,678,133 B2 | 3/2010 | Modesitt | |
| 2002/0099390 A1 * | 7/2002 | Kaplan et al. | 606/139 |
| 2002/0103459 A1 * | 8/2002 | Sparks et al. | 604/164.13 |

(Continued)

FOREIGN PATENT DOCUMENTS

WO    WO 97/13463    4/1997

(Continued)

OTHER PUBLICATIONS

International Search Report, Nov. 22, 2006, 5 pgs.

(Continued)

Primary Examiner—Darwin P Erezo
Assistant Examiner—Christina Lauer
(74) Attorney, Agent, or Firm—Brooks, Cameron & Huebsch, PLLC

(57) ABSTRACT

Methods, apparatus, and systems for locating a patent foramen ovale (PFO) with a positioning device that can be configured to occlude the PFO. Methods, apparatus, and systems include the use of a positioning device that can be seated on the limbus of a septum secundum (SS). The positioning device includes a piercing member that can pierce the SS and a septum primum.

28 Claims, 13 Drawing Sheets

U.S. PATENT DOCUMENTS

| | | | |
|---|---|---|---|
| 2002/0107531 A1 | 8/2002 | Schreck et al. | |
| 2002/0173688 A1 | 11/2002 | Chen et al. | |
| 2002/0183787 A1 | 12/2002 | Wahr et al. | |
| 2003/0013971 A1 | 1/2003 | Makin et al. | |
| 2003/0045901 A1 | 3/2003 | Opolski | |
| 2003/0050665 A1 | 3/2003 | Ginn | |
| 2003/0144694 A1 | 7/2003 | Chanduszko et al. | |
| 2003/0181945 A1 | 9/2003 | Opolski et al. | |
| 2003/0191495 A1 | 10/2003 | Ryan et al. | |
| 2003/0208232 A1 | 11/2003 | Blaeser et al. | |
| 2003/0216759 A1* | 11/2003 | Burbank et al. | 606/157 |
| 2003/0225421 A1 | 12/2003 | Peavey et al. | |
| 2004/0073242 A1 | 4/2004 | Chanduszko | |
| 2004/0087968 A1 | 5/2004 | Core | |
| 2004/0092973 A1 | 5/2004 | Chanduszko | |
| 2004/0093017 A1 | 5/2004 | Chanduszko | |
| 2004/0098121 A1 | 5/2004 | Opolski | |
| 2004/0127855 A1 | 7/2004 | Core | |
| 2004/0127917 A1 | 7/2004 | Ginn | |
| 2004/0133236 A1 | 7/2004 | Chanduszko | |
| 2004/0158264 A1 | 8/2004 | Adams et al. | |
| 2004/0176788 A1 | 9/2004 | Opolski | |
| 2004/0176797 A1 | 9/2004 | Opolski | |
| 2004/0176799 A1 | 9/2004 | Chanduszko et al. | |
| 2004/0193147 A1 | 9/2004 | Malecki et al. | |
| 2004/0230185 A1 | 11/2004 | Malecki et al. | |
| 2004/0243122 A1 | 12/2004 | Auth et al. | |
| 2004/0267191 A1* | 12/2004 | Gifford et al. | 604/22 |
| 2004/0267306 A1 | 12/2004 | Blaeser et al. | |
| 2005/0021016 A1 | 1/2005 | Malecki et al. | |
| 2005/0034735 A1 | 2/2005 | Deem et al. | |
| 2005/0043759 A1 | 2/2005 | Chanduszko | |
| 2005/0059983 A1 | 3/2005 | Opolski et al. | |
| 2005/0059984 A1 | 3/2005 | Chanduszko et al. | |
| 2005/0070923 A1 | 3/2005 | McIntosh | |
| 2005/0070952 A1 | 3/2005 | Devellian | |
| 2005/0080406 A1 | 4/2005 | Malecki et al. | |
| 2005/0080430 A1 | 4/2005 | Wright, Jr. et al. | |
| 2005/0085843 A1 | 4/2005 | Opolski et al. | |
| 2005/0101984 A1 | 5/2005 | Chanduszko et al. | |
| 2005/0119524 A1* | 6/2005 | Sekine et al. | 600/114 |
| 2005/0131401 A1 | 6/2005 | Malecki et al. | |
| 2005/0131460 A1 | 6/2005 | Gifford, III et al. | |
| 2005/0228283 A1 | 10/2005 | Gifford et al. | |
| 2005/0251210 A1* | 11/2005 | Westra et al. | 606/232 |
| 2005/0267495 A1 | 12/2005 | Ginn et al. | |
| 2007/0043337 A1 | 2/2007 | McAuley | |
| 2007/0060858 A1 | 3/2007 | Sogard et al. | |

FOREIGN PATENT DOCUMENTS

| | | |
|---|---|---|
| WO | WO 02/17809 | 3/2002 |
| WO | WO 2005/027753 | 3/2005 |
| WO | 2005039419 | 5/2005 |

OTHER PUBLICATIONS

International Search Report, Dec. 1, 2006, 8 pgs.

* cited by examiner

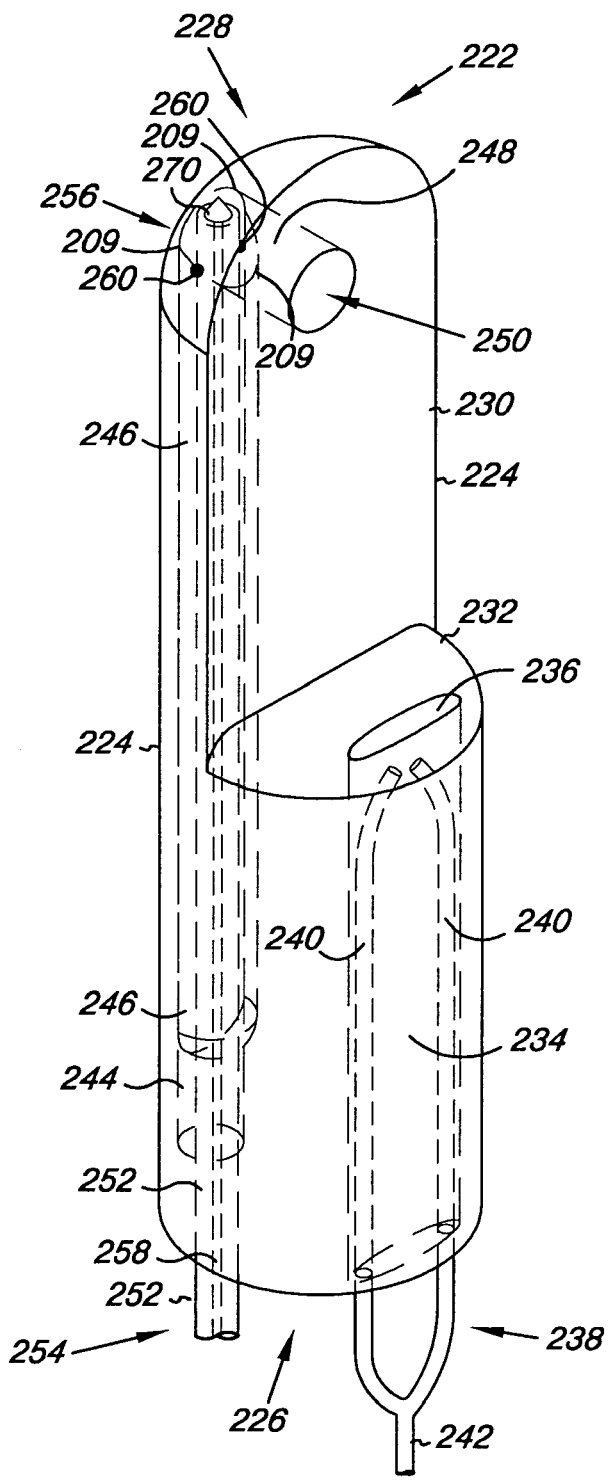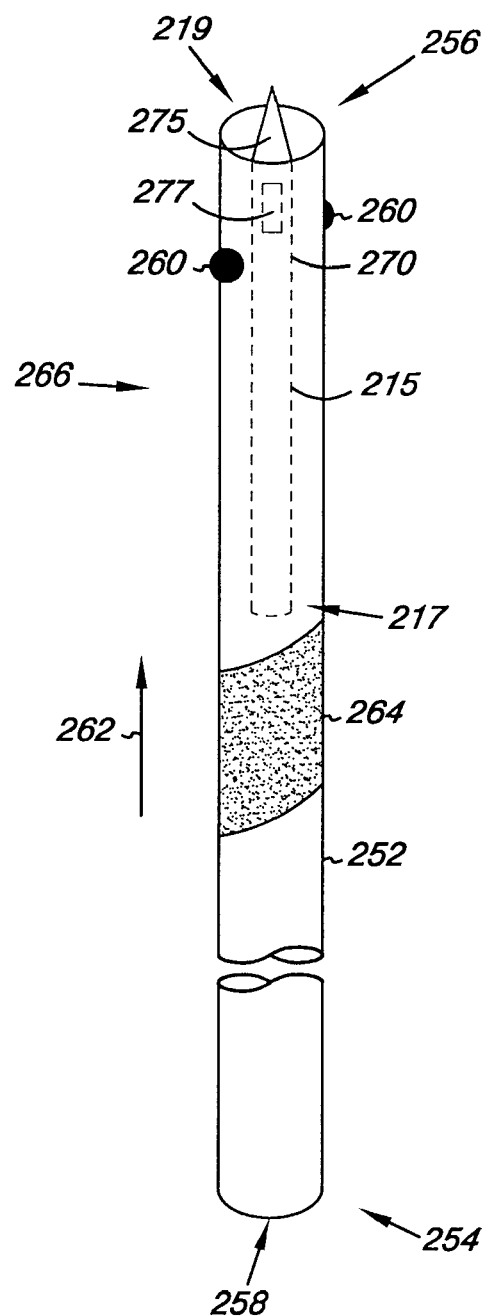
Fig. 2A
Fig. 2B

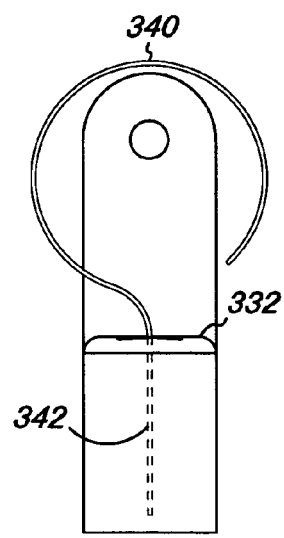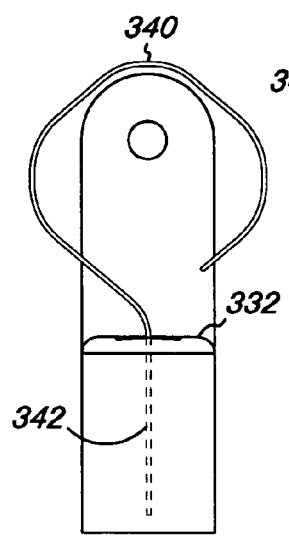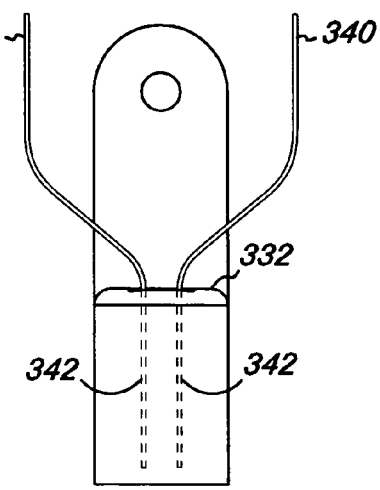
Fig. 3A    Fig. 3B    Fig. 3C
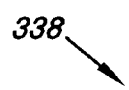
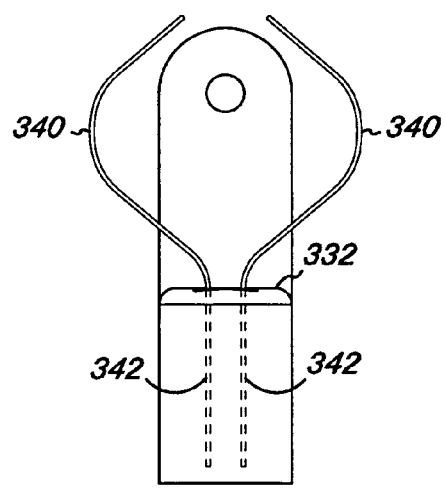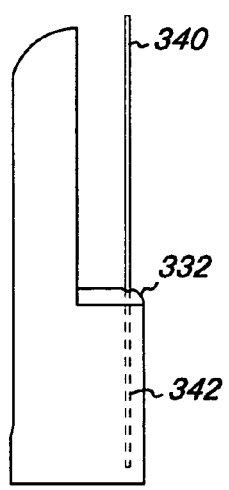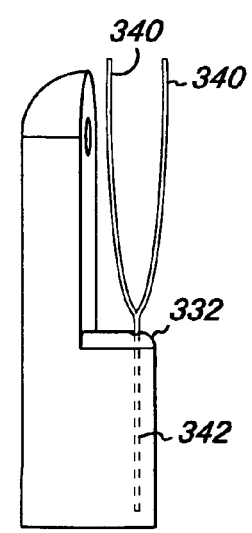
Fig. 3D    Fig. 3E    Fig. 3F

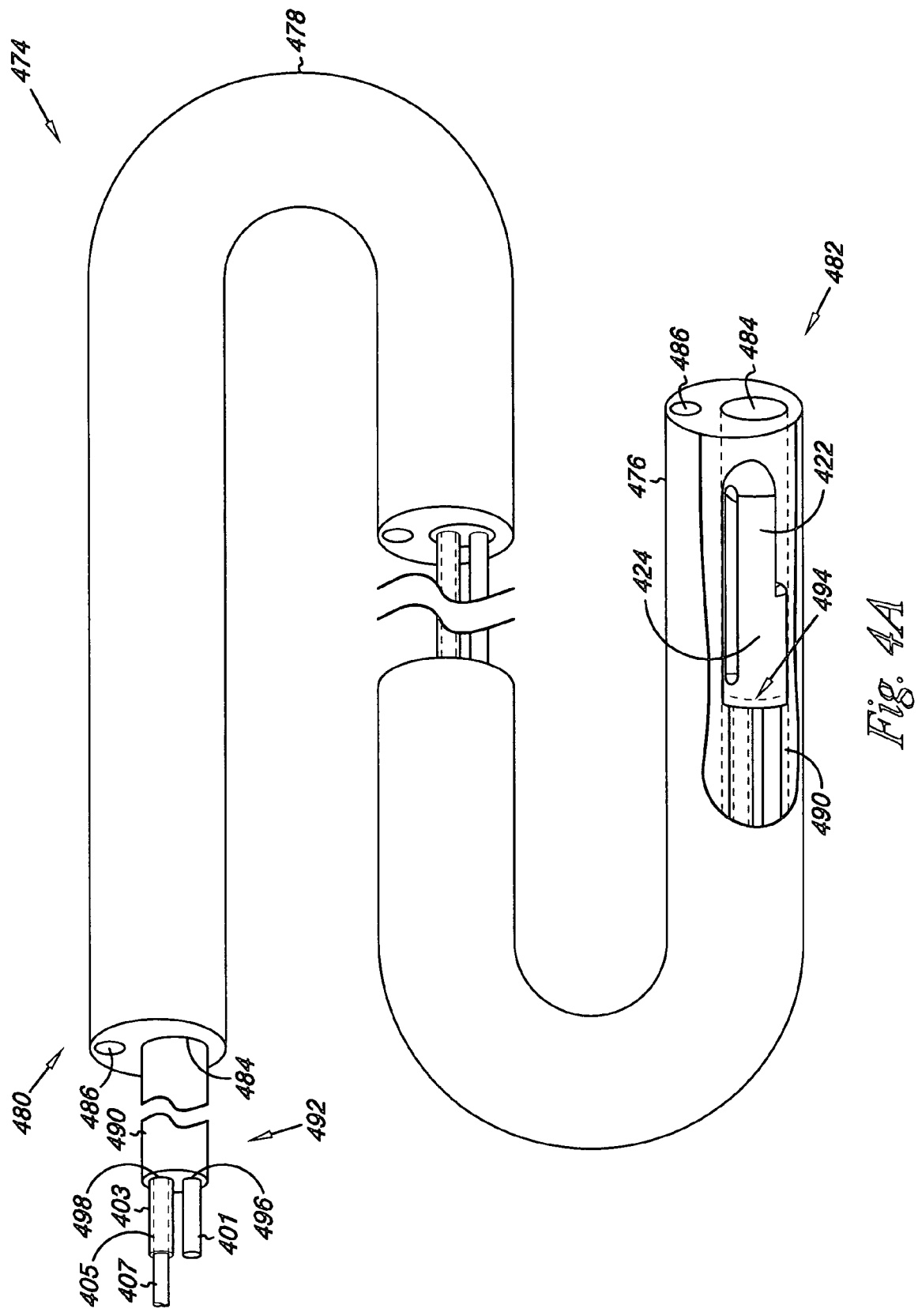

TRANSEPTAL APPARATUS, SYSTEM, AND METHOD

FIELD OF THE INVENTION

The present invention relates generally to apparatus, systems, and methods for use in a heart, more particularly to apparatus, systems, and methods for locating a PFO with a positioning device that can be configured to occlude the PFO.

BACKGROUND

The human heart is divided into four chambers. These include the right atrium, the right ventricle, the left atrium, and the left ventricle. The right atrium and right ventricle are divided from the left atrium and left ventricle by a muscular wall called the septum. The atrial septum is the wall separating the atria, and the ventricular septum is the wall separating the ventricles.

Early in fetal development the two atria (i.e., left and right atriums) are a single chamber. A wall or membranous structure develops from the superior aspect of the atrial chamber and extends superiorly toward the base of the atrial chamber. This membrane is the septum primum (SP). As the SP seals to the base of the chamber, it is dissolved away at the superior attachment, creating a passageway for blood to travel from the right atria to the left atria (bypassing the developing lungs). At about the same time, a second membrane develops from the superior aspect of the right atrium and extends inferiorly. This membrane is the septum secundum (SS). It fuses with the SP along the walls of the atria, but does not extend to the base of the atria. The inferior portion of the SS is named the limbus. The two membranes form a passage defined by thin tissue (SP) and thick tissue (SS) that extends from the right atria to the left atria. This passage is named the foramen ovale. The portion of the SP that comprises the left side of the foramen ovale is named the fossa ovalis. The limbus of the SS is distinct from the fossa ovalis of the SP in that it is thicker and more muscular.

Upon birth blood must be diverted into the lungs of the newborn. One event that enables this is an increase in pressure within the left atrium relative to the right atrium. This pressure reversal effectively closes the foramen ovale and eliminates the shunting of blood from right to left. In most people, the SP and SS membranes that form the passage of the shunt fuse and the passage is eliminated. However, in a minority of people, these membranes do not fuse effectively and the shunt remains sealed by pressure, but the passage remains viable, or patent. This condition is named patent foramen ovale (PFO). In unusual circumstances the pressure in the right atrium can exceed that in the left atrium, allowing passage of blood through the PFO. This would typically be inconsequential, except when the venous (right atrial) blood contains thrombotic debris that is normally eliminated by thrombolytic mechanisms in the lungs. In this case, a clot can travel to the left atria and become an embolic risk to the patient's health through myocardial infarction or stroke.

BRIEF DESCRIPTION OF THE DRAWINGS

FIG. 2A illustrates a positioning device according to one embodiment of the present invention.

FIG. 2B illustrates an elongate structure of the positioning device in a first position according to one embodiment of the present invention.

FIGS. 3A-3F illustrate extension members of the positioning device according to various embodiments of the present invention.

FIGS. 4A-4C illustrate various embodiments of a system according to the teachings of the present invention.

DETAILED DESCRIPTION

Figure 1:
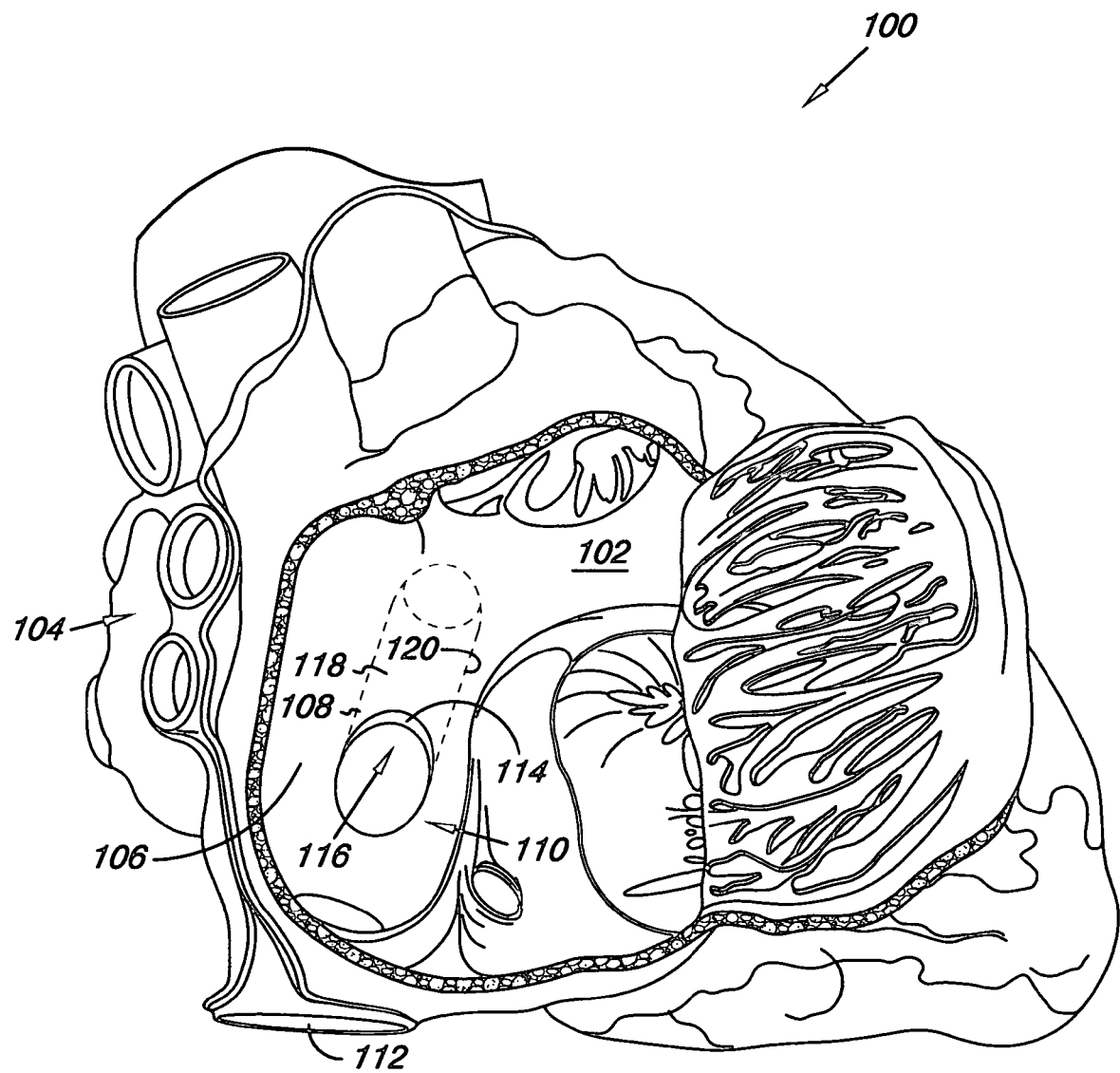
FIG. 1 illustrates an embodiment of a right lateral view of the heart.

Embodiments of the present invention are directed to methods, apparatus, and systems for locating a PFO with a positioning device that can be configured to occlude the PFO. As will be discussed in more detail herein, a positioning device on a delivery catheter can be seated on the septum secundum (SS) of the atrial septum, e.g., seated on the limbus of the SS. Seating the positioning device on the SS helps to locate the positioning device at a position on the atrial septum where two membranes, the SS and the septum primum (SP), lie parallel to one another. This position makes possible the use of the various embodiments described herein to prepare a PFO for occlusion and to introduce various components of the positioning device to the left atrium from the right atrium. For example, in various embodiments, the SS or the SS and the SP can be pierced with a piercing member that extends from an elongate structure of the positioning device and into the left atrium.

In some embodiments, the positioning device can include extension members that can be used to tighten thin tissue of the SP and/or thick tissue of the SS within the passage of a PFO prior to piercing those tissues. Thus, in various embodiments, by manipulating components of the positioning device (e.g., extension members and/or elongate structure and piercing member) thick and/or thin tissue can be tightened and pierced.

In various embodiments, the positioning device can include an extension member that can extend into the passage of the PFO while the elongate body of the positioning device remains in the right atrium. The extension member assures that the elongate body of the device is correctly oriented with respect to the passage of the PFO. This positioning mechanism assures correct alignment for a piercing member contained within the elongate structure of the positioning device.

In various embodiments, the positioning device can be used as a transeptal delivery device for introducing devices such as therapeutic and diagnostic devices, solids, fluids, substances, and the like, from a first heart chamber to a second heart chamber (e.g., from right atrium to left atrium). These and other embodiments of the present invention are discussed herein.

The Figures herein follow a numbering convention in which the first digit or digits correspond to the drawing Figure number and the remaining digits identify an element or component in the drawing. Similar elements or components between different figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide a number of additional embodiments of the positioning device according to the present invention.

In FIG. 1, a right lateral view of the heart 100 is shown with an opened right atrium 102. The heart 100 is divided into four chambers, which are referred to herein as the right atrium 102, a right ventricle, a left atrium 104 and a left ventricle. Heart 100 also includes a septal wall 106 that divides the four chambers of the heart. The portion of the septal wall dividing the left and right atriums 102 and 104 is called the interatrial septum 108. The portion of the septal wall 106 dividing the left and right ventricle is called the ventricular septum.

As shown in FIG. 1, the fossa ovalis 110 is situated at the lower part of the atrial septum 108, above and to the left of the orifice of the inferior vena cava 112. The limbus 114 of the fossa ovalis 110 is the pronounced anterosuperior margin of the fossa ovalis 110 within the right side (i.e., the right atrium 102) of the interatrial septum 108. It represents the inferior margin of the SS during fetal life.

The passage 116 can be defined by surfaces of the SS (thick tissue) and surfaces of the SP (thin tissue) and extends between the right and left atriums 102 and 104. As used herein, the passage 116 is defined by surfaces of the SS and SP and can be used interchangeably with a PFO. The thick tissue 118 forms the right margin of the passage 116 and comprises the superior portion of the interatrial septum 108. Thus, the thick tissue 118 is located adjacent the limbus 114 and extends upward and rightward away from the limbus 114. The thin tissue 120 forms the left margin of the passage 116 and comprises the inferior portion of the interatrial septum 108 (i.e., below the thick tissue 118) and extends upward and rightward substantially parallel to the thick tissue 118 and toward the left atrium 104.

Figure 2C:
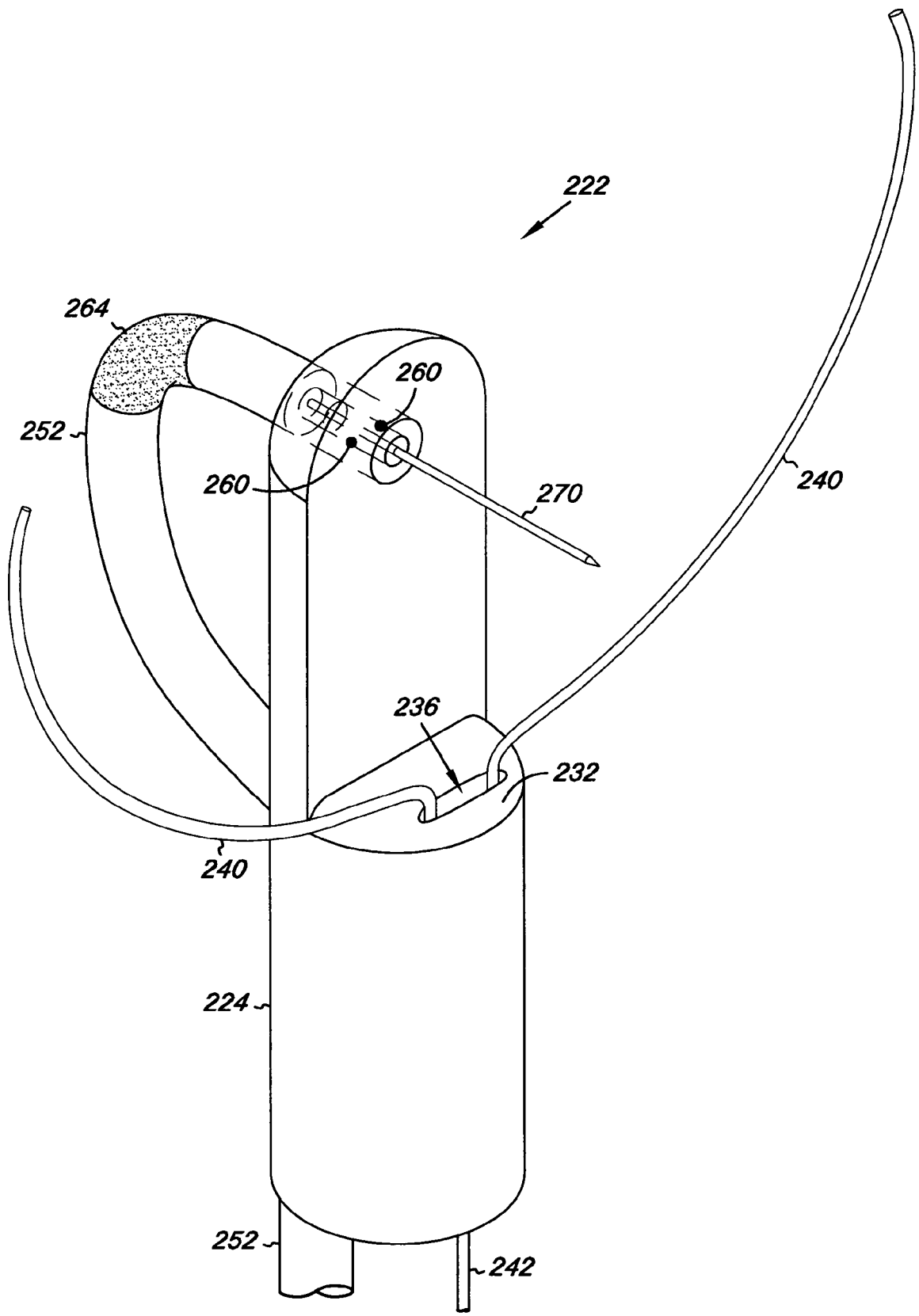
FIG. 2C illustrates the positioning device according to an additional embodiment of the present invention.

FIGS. 2A-2D illustrate various embodiments of the positioning device 222 that can be used to pierce thick and thin tissue according to the teachings of the present invention. FIG. 2A provides an illustration of a positioning device 222 according to the teachings of the present invention. As shown in FIG. 2A, positioning device 222 includes an elongate body 224 having a proximal end 226 and a distal end 228. The elongate body 224 includes a wall 230 that extends from the distal end 228 toward the proximal end 226. In the embodiment shown in FIG. 2A, the wall 230 includes a planar surface. However, in various embodiments, the wall 230 can include other types of surfaces. For example, in some embodiments, the wall 230 can include non-planar surfaces such as a convex surface or a concave surface.

The wall 230 extends toward the proximal end 226 to a ledge 232 that extends away from the wall 230. In one embodiment, the ledge 232 extends perpendicularly away from the wall 230 for a predetermined distance. The ledge 232 includes a planar surface whose outer edge defines a semicircular shape. As will be discussed herein, the ledge 232 of the positioning device 222 allows the positioning device 222 to be seated on the limbus of the SS of a patient's heart.

Since the size and shape of the limbus can vary from patient to patient, the positioning device 222, including the wall 230 and the ledge 232 can include various shapes and sizes that can be based on the anatomical structures of a patient's heart including the limbus of the SS. For example, in some embodiments, the ledge 232 can have a surface defining various geometric shapes and sizes, including, but not limited to, convex shapes, concave shapes, recessed shapes, and irregular shapes, among others. In addition, in some embodiments, the ledge 232 can extend at various angles other than perpendicular from the wall 230 of the elongate body 224.

The positioning device 222 includes a number of lumens that extend various lengths within the positioning device 222. In one embodiment, a first lumen 234 extends toward the ledge 232. As shown in FIG. 2A, the first lumen 234 extends toward ledge 232 and communicates with a ledge opening 236 defined by the surface of the ledge 232. In one embodiment, the first lumen 234 and the ledge opening 236 can accommodate the movement of a component positioned within the first lumen 234, as will be discussed herein.

As shown in FIG. 2A, the first lumen 234 includes surfaces defining an ovular cross-sectional shape. In various embodiments however, the first lumen 234 can include other cross-sectional shapes including, but not limited to, circular and polygonal cross-sectional shapes. In various embodiments, the cross-sectional shape of the first lumen 234 can be formed to accommodate a particular design of a component therein.

For example, in one embodiment, the component can be an extension member 238. As shown in FIG. 2A, the extension member 238 is extendably positioned within the first lumen 234 toward the ledge 232 of the elongate body 224. As used herein, an extendably positioned extension member 238 is an extension member having at least one arm 240 that can be moved within the first lumen 234 and through the ledge opening 236 such that the arm 240 extends away from the ledge 232 of the elongate body 224. In various embodiments, the arm 240 can extend away from the ledge 232 in various directions and in various planes, as will be discussed herein with respect to FIG. 3A.

In various embodiments, the extension member 238 can include one or more arms and one or more bases. For example, in some embodiments, the extension member 238 can include two arms and two bases. And, in other embodiments, the extension member can include a single arm and a single base, as will be discussed herein with respect to FIGS. 3A-3F.

In the embodiments illustrated in FIGS. 2A and 2C, the extension member 238 includes two arms 240 that diverge from a base 242. The two arms 240 extend away from the ledge 232 both longitudinally and radially when moved through the ledge opening 236, as shown in FIG. 2C.

In one embodiment, the arms 240 have a predefined shape in their relaxed state, as illustrated in FIG. 2C. When retracted within the first lumen 234, the arms 240 elastically bend so as to be held in compression within the first lumen 234. As the arms 240 extend from the first lumen 234, the arms 240 return towards their predefined shape. As will be discussed herein, as the arms 240 return towards their predefined shape they can help to impart an expansion force upon tissue forming defining the passage of a PFO in a manner that stretches the tissue of the passage in different directions.

In various embodiments, the extension member can include a number of cross-sectional shapes. Examples of cross-sectional shapes of the extension member can include, but are not limited to, circular, ovular, and polygonal cross-sectional shapes, among others.

Examples of suitable materials for forming the extension member 238 can include, but are not limited to, metals, metal alloys, and/or polymer materials. Specific examples of such materials can include shape memory metals such as Nitinol having super elastic properties, linear elastic properties, and/or shape memory properties. Other examples can include shape memory polymers. These materials can allow for forming and setting the predefined shape in the arms 240 that can resiliently flex to be compressed within the first lumen 234 and then extend toward the predefined shape as the extension member 238 extends from the first lumen 234.

The embodiments illustrated in FIGS. 3A-3F show examples of extension members 338 having a variety of configurations. The embodiments illustrated in FIGS. 3A-3F are not meant to limit the extension members, but rather, to illustrate a few of the many types of extension member that are contemplated by this disclosure.

As shown in FIGS. 3A and 3B, the extension member 338 includes a single arm 340 and a single base 342. In some embodiments, the extension member can include a number of arms and a number of bases. As shown in the embodiments illustrated in FIGS. 3C and 3D, the extension member 338 includes two arms 340 and two bases 342. In these embodiments, each arm 340 includes a base 342.

When the extension member 338 extends from the ledge 332, the arm or arms, depending upon the particular configuration of the extension member, can extend away in a single plane. For example, the embodiment illustrated in FIG. 3E includes a side view of an extension member 338 having two arms 340 and a single base 342. The extension member 338 illustrated in FIG. 3E is shown extending away from the ledge 332 of the elongate body 324 within the same plane. Since the arms 340 extend away from the ledge 332 within the same plane, and because a side view is illustrated in FIG. 3E, only one arm 340 can be seen in FIG. 3E.

In other embodiments, the extension member can extend away from the ledge in a number of different planes. For example, the embodiment illustrated in FIG. 3F illustrates a side view of an extension member 338 having two arms 340 and a single base 342. The extension member illustrated in FIG. 3F is shown extending away from the ledge 332 in two different planes. Since the arms 340 are shown as extending away from the ledge 332 in two different planes, and because a side view is illustrated in FIG. 3F, the two arms 340 of the extension member 338 can be seen in FIG. 3F.

Referring again to FIG. 2A, the positioning device 222 can include a second lumen 244. In various embodiments, the second lumen 244 can extend toward the distal end 228 of the elongate body 224. In the embodiment illustrated in FIG. 2A, the second lumen 244 extends toward the distal end 228 of the elongate body 224 to communicate with a channel 246. In this embodiment, the length of the second lumen 244 is short relative to the first lumen 234. In various embodiments however, the length of the second lumen 244 can be substantially longer as will be discussed herein.

The channel 246 is defined by the surface of the elongate body 224 and extends longitudinally between the second lumen 244 and a third lumen 248.

The third lumen 248 extends from a wall opening 250, which is defined by the surface of the wall 230. The third lumen 248 extends from the wall opening 250 completely through the elongate body 234 to a transverse opening 209 to define the third lumen 248. In one embodiment, the third lumen 248 extends through the elongate body to communicate with the channel 246, as discussed herein. In various embodiments, the third lumen 248 is perpendicular relative to the second lumen 244 and the channel 246. However, in some embodiments, the third lumen 248 can be angled other than perpendicular relative to the second lumen 244 and the channel 246. And, in some embodiments, the third lumen can include curved surfaces that define a rotation point, as will be discussed more fully herein.

In the embodiments described herein, the second lumen 244, the channel 246, and the third lumen 248 can form a contiguous conduit in which components of the positioning device 222 can be positioned, extended, and/or retracted. For example, one such component can include an elongate structure 252, as illustrated in FIGS. 2A-2D. The elongate structure 252 includes a proximal end 254 and a distal end 256. The elongate structure 252 also includes a lumen 258 that extends longitudinally between the proximal end 254 and the distal end 256 of the elongate structure 252. In various embodiments, the elongate structure 252 can be extendably positioned within the second lumen 244 of the elongate body 224 toward the distal end 228 of the elongate body 224. In such embodiments, the elongate structure 252 passes through the second lumen 244, the channel 246, and to the third lumen 248, as shown in FIG. 2A.

In various embodiments, the elongate structure 252 can include a rotation point 260 along which the distal end 256 of the elongate structure 252 can rotate. As shown in FIGS. 2A-2D, the rotation point 260 includes two pivots coupled to an outer surface of the elongate structure 252. In turn, the pivots can be rotatably coupled to surfaces defining the channel 246 proximal the distal end 228 of the elongate body 224. In an alternative embodiment, the rotation point 258 can be defined by surfaces of the third lumen 248. In the alternative embodiment, the surfaces of the third lumen 248 can be formed to provide the rotation point 260 along which the distal end 256 of the elongate structure 252 can rotate. In such an embodiment, the elongate structure 252 would not require pivots.

The elongate structure 252 can include a flexible portion 264. The flexible portion 264 can be configured as a region of the elongate structure 252 that is more flexible as compared to other portions of the elongate structure 252. For example, in some embodiments, the flexible portion 264 of the elongate structure 252 can be formed of a flexible plastic and/or metal that can bend without obstructing the lumen 258 of the elongate structure 252. A portion of the elongate structure 252 extending from the flexible portion 264 toward the proximal end 254 of the elongate structure 252 can be formed of a semi-flexible plastic and/or metal that can bend, but not as easily as the flexible portion 264. And, a portion of the elongate structure 252 extending from the flexible portion 264 toward the distal end 256 of the elongate structure can be formed of a substantially rigid plastic and/or metal so as not to bend.

In the embodiments described herein, the rotation of the elongate structure 252 is accompanied by a predetermined bend of the elongate structure 252. That is, the rotation occurs along the rotation point 260 and the predetermined bend occurs along the flexible portion 264 of the elongate structure 252.

Figure 2D:
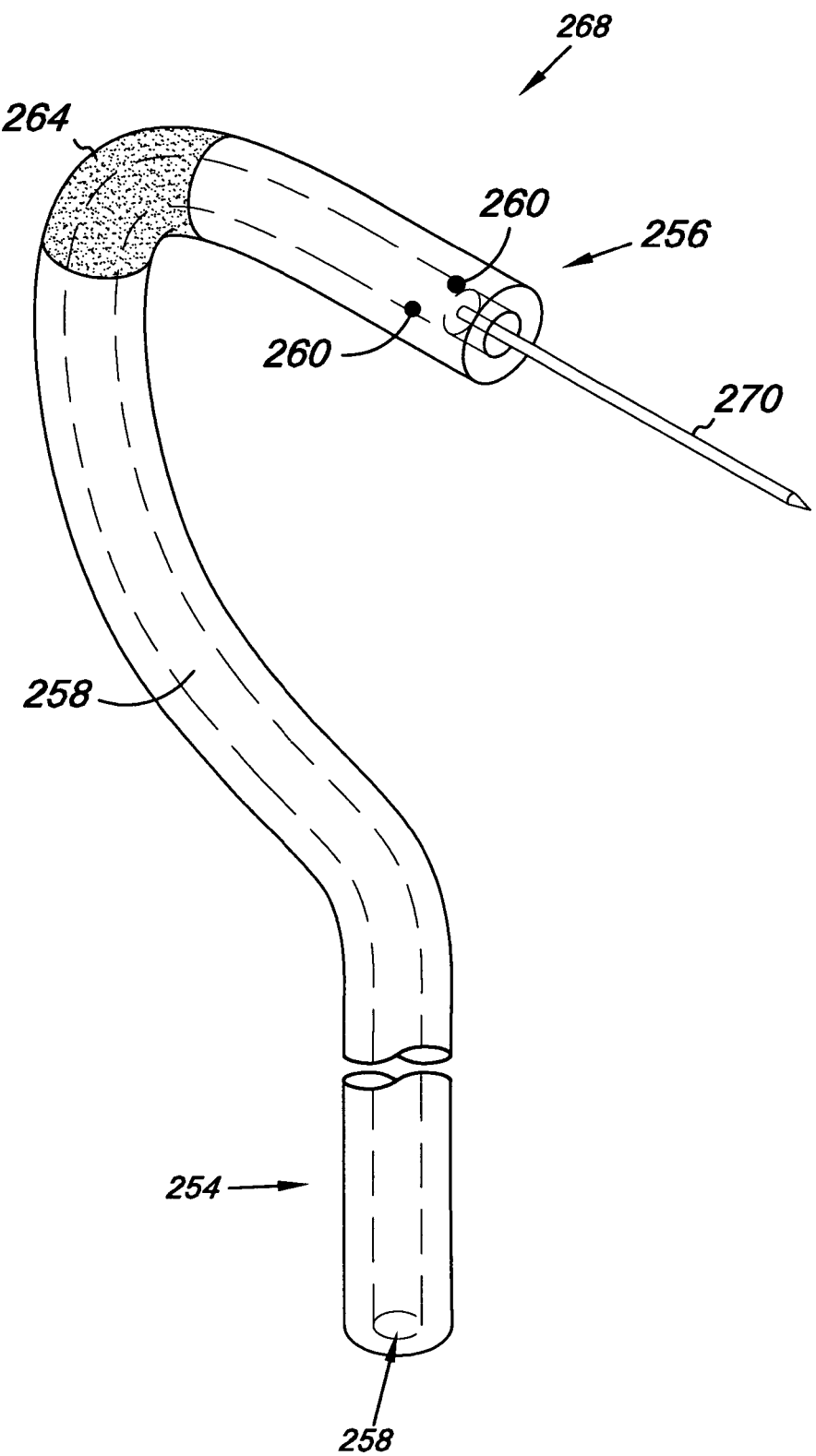
FIG. 2D illustrates the elongate structure of the positioning device in a second position according to one embodiment of the present invention.

The following description provides one example of the rotation and the bending of the elongate structure 252. In FIGS. 2A and 2B the elongate structure 252 is illustrated in a first position 266. In FIGS. 2C and 2D, the elongate structure 252 is illustrated in a second position 268. For ease of illustration, FIGS. 2B and 2D illustrate the elongate structure 252 separated from the elongate body 224 of the positioning device 222.

In the first position 266, the elongate structure 252 is extendably positioned within the second lumen 244, the channel 246, and the third lumen 248 of the elongate body 224, as discussed herein. In the second position 268 (e.g., FIGS. 2C and 2D), the elongate structure 252 extends away from the channel 246. In addition, the second position 268 also illustrates the predetermined bend at the flexible portion 264, as well as the rotation of the elongate structure along the rotation point 260. As shown in FIG. 2C, a portion of the elongate structure 252 proximal to and at the distal end 256 is rotated substantially 90 degrees relative to the elongate body 224. As will be discussed herein, rotating the elongate structure substantially 90 degrees positions a piercing member substantially perpendicular to the thick tissue (i.e., septum secundum). However, in various embodiments, the elongate structure 252 can be rotated more than 90 degrees and less than 90 degrees.

In one embodiment, the movement from the first position 266 to the second position 268 can result from a compression force, indicated by arrow 262 in FIG. 2B, applied to the elongate structure 252. As used herein, the compression force is a force applied through the elongate structure 252 to impart compression on the rotation point 260 of the elongate structure 252. The compression force can originate from the proximal end 254 of the elongate structure 252 by a pushing force applied to the elongate structure at the proximal end 254 of the elongate structure 252.

To move from the first position 266, as shown in FIG. 2B, to the second position 268, as shown in FIG. 2D, the pushing force can be applied by a deployment shaft, as will be discussed herein, towards the proximal end 254 of the elongate structure 252. Pushing force applied to the deployment shaft acts on the pivots of the rotation point 260. As the compression force increases, a result of increasing the pushing force at the proximal end 254, a column strength of the elongate structure is eventually overcome such that the flexible portion 264 of the elongate structure 252 begins to bend relative the remainder of the elongate structure 252. As the flexible portion 264 begins to bend, the elongate structure 252 begins to extend away from the channel 246 of the elongate body 224. As the elongate structure 252 extends away, the predetermined bend of the flexible portion 264 begins to form as the distal end 256 of the elongate structure 252 rotates along the rotation point 260 of the elongate structure 252 to the second position 268.

At the second position 268, the distal end of the elongate structure is positioned substantially 90 degrees relative to the elongate body 224 and is temporarily locked in the second position 268. Locking the elongate structure in the second position 268 can include a number of methods. In one embodiment, for example, the deployment shaft used to apply the pushing force can be locked to prevent it from backing away from the elongate structure, and thus releasing the pushing force acting on the elongate structure.

To move from the second position 268 to the first position 266, a pulling force can be applied to the proximal end 254 of the elongate structure 252 to pull the elongate structure 252 from the second position 268 to the first position 266. For example, in some embodiments, the pulling force can be the result of pulling the proximal end 254 of the elongate structure 252 with the deployment shaft, as will also be discussed herein.

As shown in FIG. 2B, in various embodiments, a piercing member 270 can be slidably positioned within the lumen 258 of the elongate structure 252. The piercing member 270 includes an elongate body 215 having a proximal and a distal end 217 and 219. In various embodiments, the proximal end 217 can include a structure that can penetrate tissue, such as a pointed, tapered, etc., structure. In various embodiments, the piercing member 270 can be formed of a number of materials such as metals, metal alloys, polymers, shape memory metals and polymers, and others.

In various embodiments, the piercing member can includes a therapeutic device 275. For example, in various embodiments, the distal end of the piercing member can be used to pierce the SS and SP to induce trauma to those tissues such that when they are in contact and begin to heal, they can fasten to each other to effectively occlude a PFO. In other embodiments, a therapeutic device, such as sutures, can be coupled to the piercing member 270 and the piercing member can be used to pierce the SS and SP to stitch the tissues together to effectively occlude a PFO.

In various embodiments, the piercing member can include a diagnostic device 277. Such diagnostic devices can include pressure sensors, optical sensors, oxygen sensors etc. In one embodiment, a pressure sensor 277 can be coupled to the piercing member 270 and advanced into the left atrium to aid in the measurement of pressure in the left atrium relative to the left ventricle and vice versa to help with diagnosing valve problems, e.g., a defective native or artificial mitral valve. In such an embodiment, the piercing member 270 can be advanced to the left ventricle via the mitral valve to determine pressure in the left ventricle.

In various embodiments, the piercing member 270 can be positioned proximal the distal end 256 of the elongate structure 252, as shown in FIGS. 2A and 2B. In various embodiments, piercing member 270 can be moved within the lumen 258 of the elongate structure 252 such that a portion of the piercing member 270 moves through the wall opening 250 and away from the wall 230, as shown in FIGS. 2C and 2D. As will be discussed below with respect to FIGS. 5A-5E, the piercing member 270 can be used to pierce the thick tissue of the SS and thin tissue of the SP to access the left atrium from the right atrium.

Figure 4B:
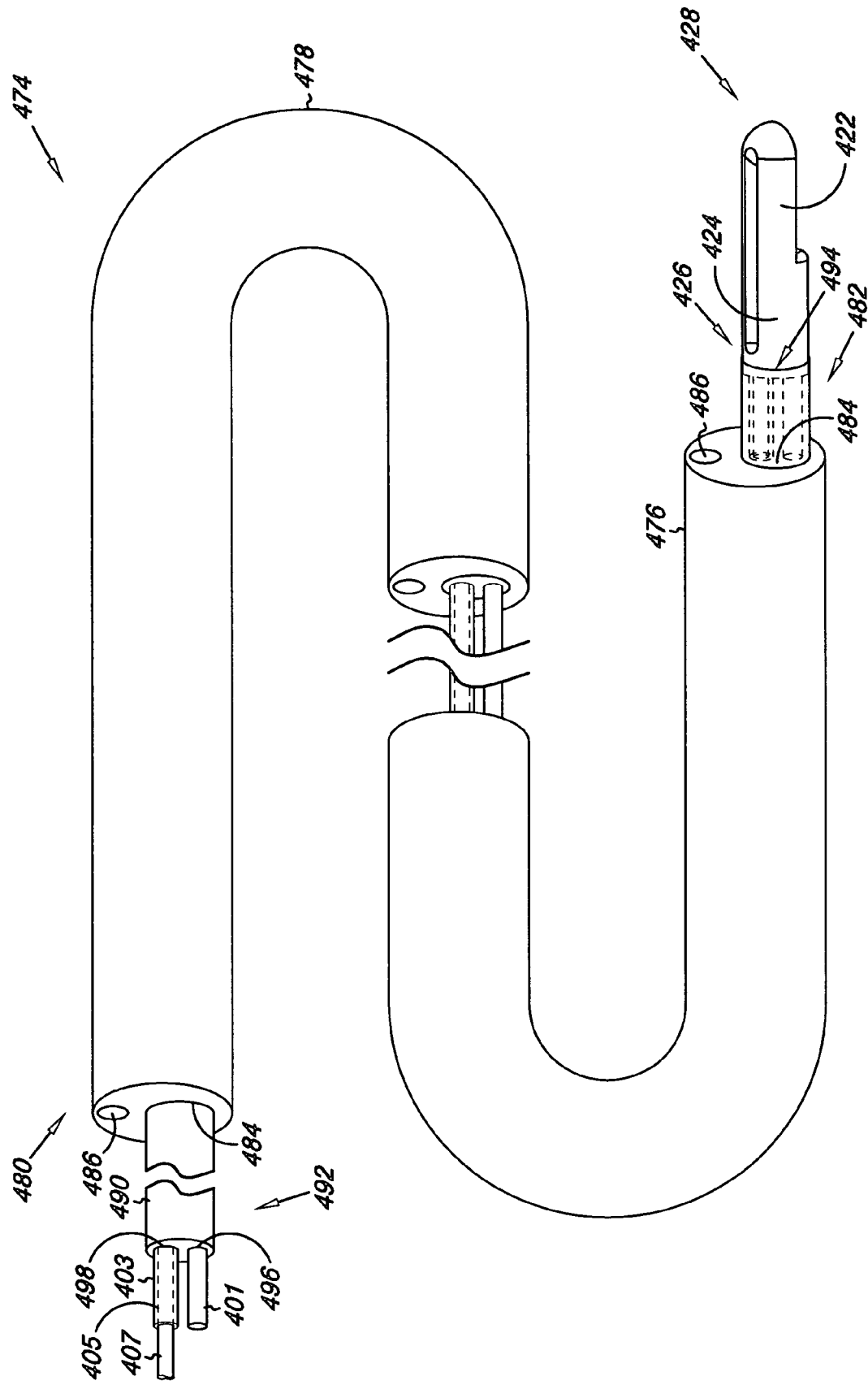
Figure 4C:
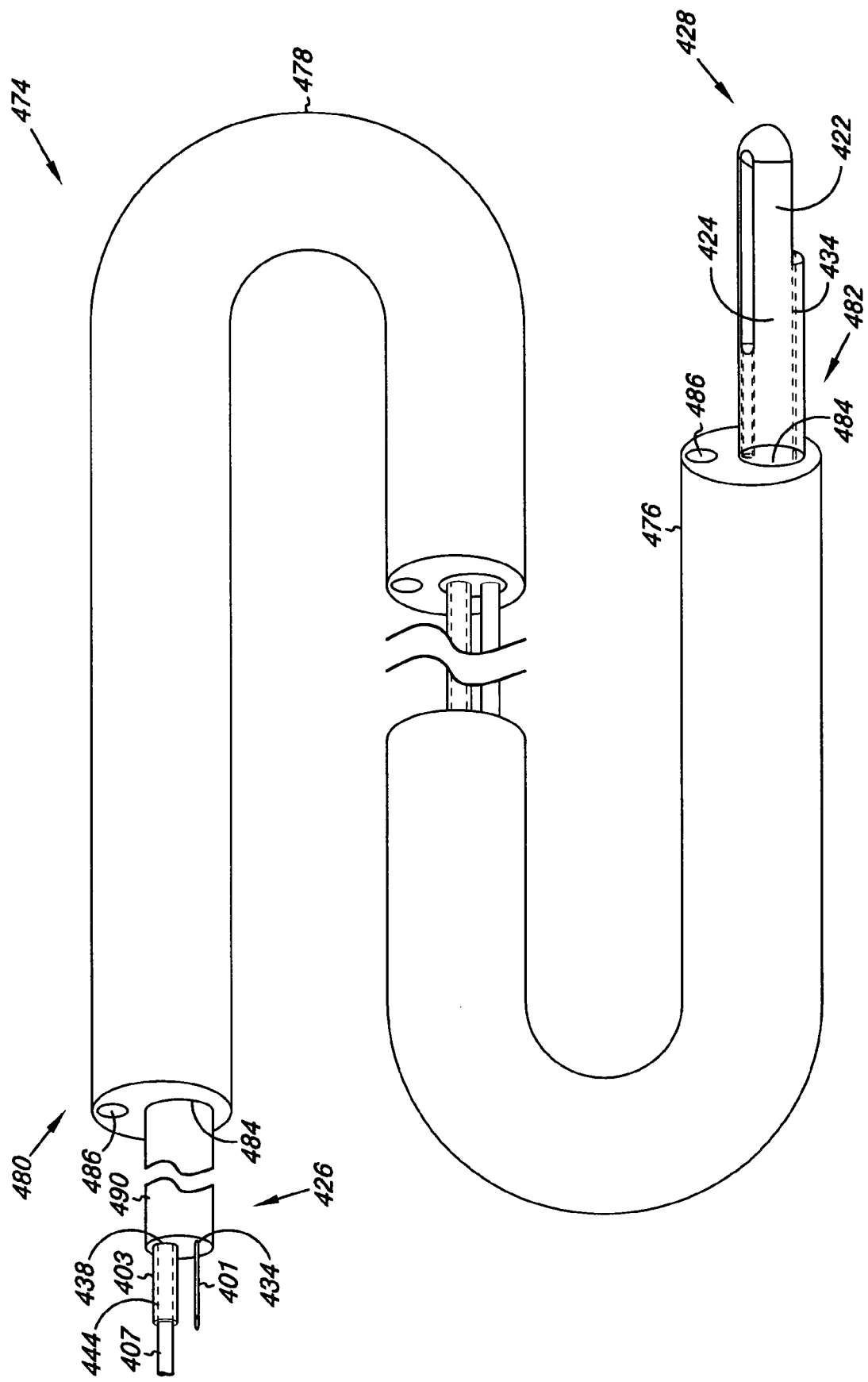

FIGS. 4A-4C illustrate various embodiments of a system 474 that includes the positioning device 422 of the present invention. As shown in FIGS. 4A and 4B, system 474 includes positioning device 422, as described herein. System 474 also includes a catheter 476. The catheter 476 includes an elongate body 478 having a proximal end 480 and a distal end 482. In various embodiments, the positioning device 422 can be located between the proximal end 480 and the distal end 482 of the catheter 476. The catheter 476 includes lumen 484. In various embodiments, the lumen 484 can extend longitudinally toward the distal end 482 of the catheter 476. In one embodiment, lumen 484 extends from the proximal end 480 to the distal end 482 of the catheter 476.

The catheter 476 can further include a guidewire lumen 486. The guidewire lumen 486 can extend within the elongate body 478 of the catheter 476 from the proximal end 480 to the distal end 482 of the catheter 476. In various embodiments, the guidewire lumen 486 can receive a guidewire for positioning the catheter 476 and the positioning device 422 within a heart chamber (e.g., a right atrium of a patient).

In various embodiments, the system 474 can include a sheath 490 having proximal end 492 and a distal end 494. In some embodiments, the sheath 490 can be slidably positioned within the lumen 484 of the catheter 476. In one embodiment, the positioning device 422 can be coupled to the sheath 490 at the distal end 494 of the sheath 490. In such an embodiment, the sheath 490, including the positioning device 422 coupled thereon, can be slidably positioned with the lumen 484 of the catheter 476 to deploy the positioning device 422 from the catheter 476. In some embodiments, the positioning device can be slidably positioned within the lumen of the catheter without the sheath, as will be discussed below with respect to FIG. 4C.

The sheath 490 includes a number of lumens extending between the proximal end 492 and the distal end 494 of the sheath 490. As shown in FIGS. 4A and 4B, the sheath 490 includes a first lumen 496 and a second lumen 498. In various embodiments, the catheter 476 and the sheath 490 can include various lumen designs, e.g., coaxial, dual, triple, quadruple, etc., lumen designs. In the embodiment shown in FIGS. 4A and B, the catheter 476 includes a dual lumen design (e.g., lumen 484 and guidewire lumen 486) and the sheath 490 includes both a dual lumen design (e.g., first lumen 496 and second lumen 498) and a coaxial lumen design (e.g., third lumen 405 within second lumen 498).

In various embodiments, the first and second lumens 496 and 498 can house various components of the system 474 that move within the first and second lumens 496 and 498. For example, the system 474 can include a number of deployment shafts positioned within the first and second lumens 496 and 498. The deployment shafts can be used to deploy the various components (e.g., the elongate structure 252 shown in FIGS. 2B and 2D) of the positioning device 422 from the catheter 476. In one embodiment, the first lumen 496 of the sheath 490 includes a first deployment shaft 401 therein. The first deployment shaft 401 can be positioned adjacent the base of the extension member, as discussed herein. In such embodiments, the first deployment shaft 401 moves within the first lumen 496 of the sheath 490 and the first lumen of the elongate body 424 to extend (i.e., push) the extension member from the first lumen of the elongate body 424 of the positioning device 422.

The second lumen 498 of the sheath 490 includes a second deployment shaft 403 positioned therein. In various embodiments, the second deployment shaft 403 can be positioned adjacent the proximal end of the elongate structure, as discussed herein. In such embodiments, the second deployment shaft 403 moves within the second lumen 498 of the sheath 490 and the second lumen of the elongate body of the positioning device 422 to extend the elongate structure away from the channel of the elongate body 424, as discussed herein.

The sheath 490 can also include a third lumen 405. The third lumen 405 can include a third deployment shaft 407 positioned therein. In various embodiments, the third deployment shaft 407 can be positioned adjacent the piercing member, as discussed herein. In such an embodiment, the third deployment shaft 407 moves within the third lumen 405 of the sheath 490 and the lumen of the elongate structure to push the piercing member from the lumen of the elongate structure, as discussed herein.

FIG. 4C illustrates another embodiment of system 474. In the embodiment illustrated in FIG. 4C, the positioning device 422 is slidably positioned within the lumen 484 of the catheter 476 without the sheath. In this embodiment, the catheter 476 includes a dual lumen design and the positioning device includes lumens having both dual lumen and a coaxial lumen designs. As shown in FIG. 4C, the proximal end 426 of the positioning device 422 extends from the lumen 484 at the proximal end 480 of the catheter 476. In the embodiment illustrated in FIG. 4C, the positioning device 422 can be deployed from the distal end 482 of the catheter 476 by applying a pushing force to the proximal end 426 of the positioning device 422.

The embodiment illustrated in FIG. 4C can include a number of deployment shafts, as discussed herein. The deployment shafts can extend within the various lumens of the elongate body 424 to deploy the various components of the positioning device 422. For example, the first deployment shaft 401 can be positioned within the first lumen 434 of the elongate body 424 and adjacent the base of the extension member, as discussed herein. In such embodiments, the first deployment shaft 401 moves within the first lumen 434 of the elongate body 424 to extend the extension member from the first lumen 434 of the elongate body 424.

Additionally, the second deployment shaft 403 can be positioned adjacent the proximal end of the elongate structure, as discussed herein. In such embodiments, the second deployment shaft 403 moves within the second lumen 444 of the elongate body 424 to extend the elongate structure away from the channel, as discussed herein.

The third deployment shaft 407 can be positioned adjacent the piercing member, which is positioned within the lumen of the elongate structure, as discussed herein. In such an embodiment, the third deployment shaft 407 moves within the lumen 458 of the elongate structure 452 to extend the piercing member from the lumen 458 of the elongate structure 452.

In an alternative embodiment, some components of the positioning device do not include deployment shafts. In such an embodiment, various components of the positioning device can be deployed from the elongate body of the positioning device by manipulating the components themselves. For example, the extension member and the elongate structure can include proximal ends that extend out of the positioning device at the proximal end of the positioning device. In this configuration, a surgeon can apply a pushing force to the proximal end of the extension member, for example, to extend the extension member away from the ledge of the positioning device, as discussed herein.

The embodiments of the present invention further include methods for forming the positioning device of the present invention, as discussed herein. For example, the elongate body of the positioning device can be formed from a plastic and/or metal. The elongate body can include the proximal and distal end. In various embodiments, the wall can be formed that extends from the distal end toward the proximal end. A ledge can be formed that extends away from the wall. In various embodiments, the ledge can extend away from the wall perpendicularly or at other angles. In various embodiments, the ledge can be formed to include a surface that defines the ledge opening. Similarly, the wall can be formed to include a surface that defines the wall opening.

In various embodiments, the elongate body of the positioning device can be formed to include the first lumen, the second lumen, the channel, and the third lumen. In such embodiments, the second lumen can extend toward the distal end of the elongate body. In one embodiment, the second lumen extends between the proximal end of the elongate body and the channel.

In various embodiments, surfaces of the elongate body can be formed in such a way as to define the channel. In various embodiments, the channel can be formed to extend longitudinally between the second lumen and the third lumen. The third lumen can be formed such that it extends from the second channel and through the elongate body. In such embodiments, the third lumen meets the channel.

In various embodiments, the first lumen, the channel, and the third lumen can formed to include a contiguous conduit in which components of the positioning device can be positioned, extended, and/or retracted.

Forming the components of the positioning device can include forming the extension member such that it is extendably positioned within the first lumen toward the distal end of the positioning device. Forming the extension member can include positioning the extension member in the compressed state within the first lumen of the elongate body. Additionally, the elongate structure can be formed such that it is extendably positioned within the second lumen toward the distal end of the positioning device. The elongate structure can be formed to include a lumen that extends between the proximal end and the distal end of the elongate structure. In various embodiments, the piercing member can be formed such that it is releasably positioned within the lumen of the elongate structure proximal the distal end of the elongate structure.

Various embodiments of the present invention can include methods to locate a PFO and to access the left atrium from the right atrium by extending a piercing member through the tissue defining the PFO (i.e., the septum secundum (SS) and the septum primum (SP). Methods can also include introducing devices such as therapeutic and diagnostic devices, solids, fluids, substances, and the like, to the left atrium. Methods can also include preparing tissue defining the PFO for occlusion with the use of a closure device configured for use with the positioning device.

FIGS. 5A-5F illustrate various method embodiments that can be implemented to pierce the septum secundum (SP) and the septum primum (SP). These method embodiments describe how to seat the positioning device described herein on the limbus of the SS. In addition, these method embodiments describe how to locate and manipulate the various components of the positioning device described herein for piercing and occluding a PFO, as well as to gain entry to the left atrium.

Figure 5A:
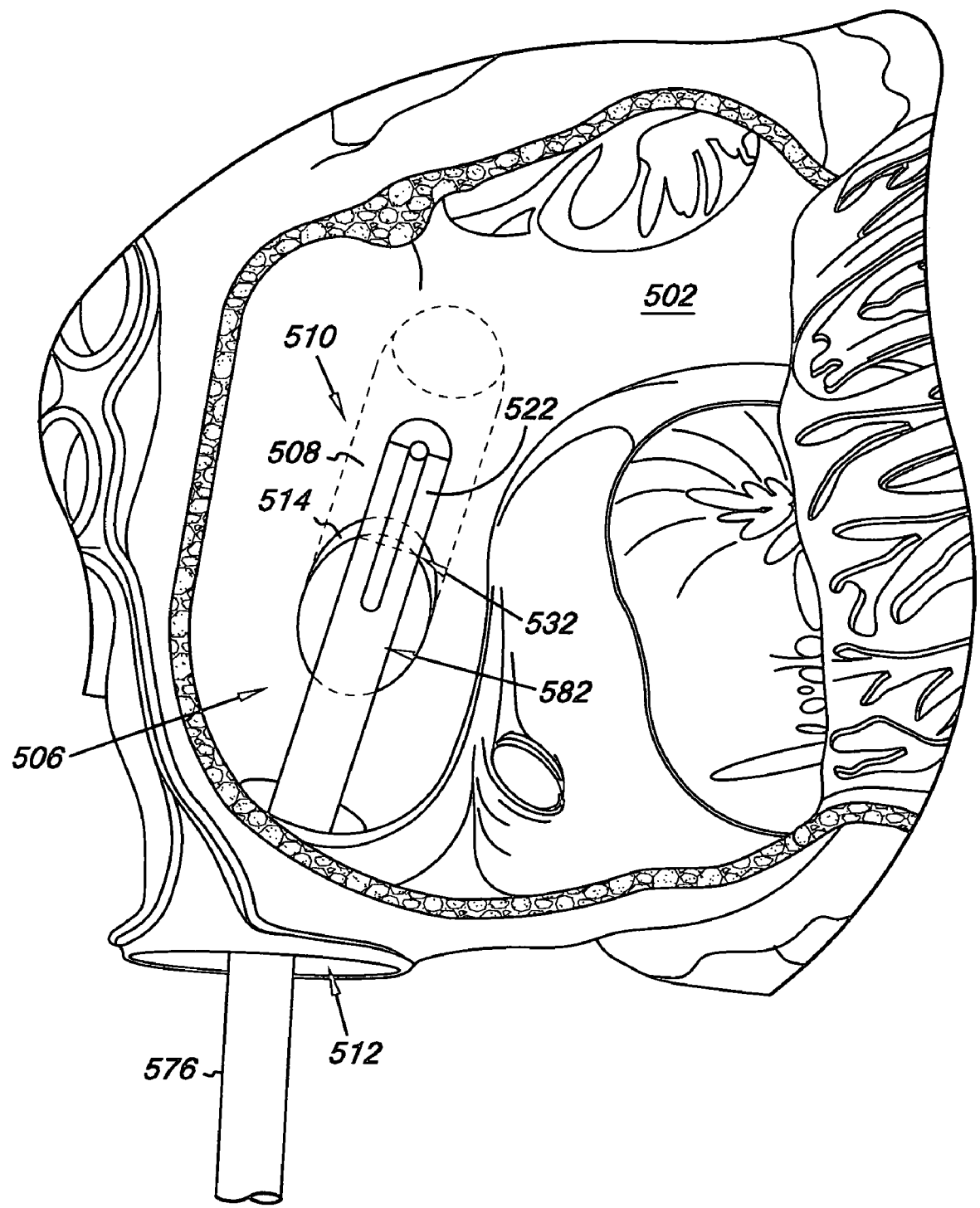
FIG. 5A illustrates the system within the right atrium of the heart according to an embodiment of the present invention.
Figure 5B:
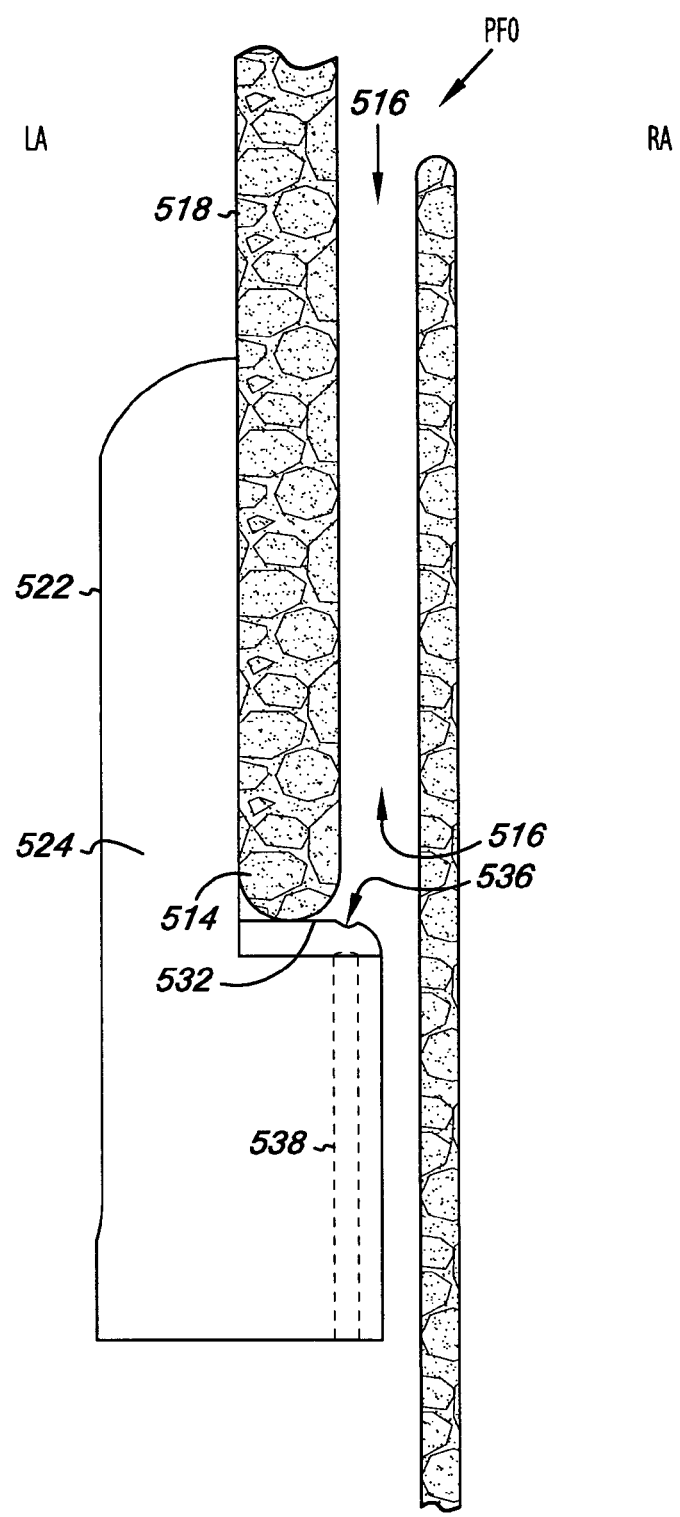
FIGS. 5B-5C illustrate the positioning device seated on the limbus of the septum secundum according to the teachings of the present invention.
Figure 5C:
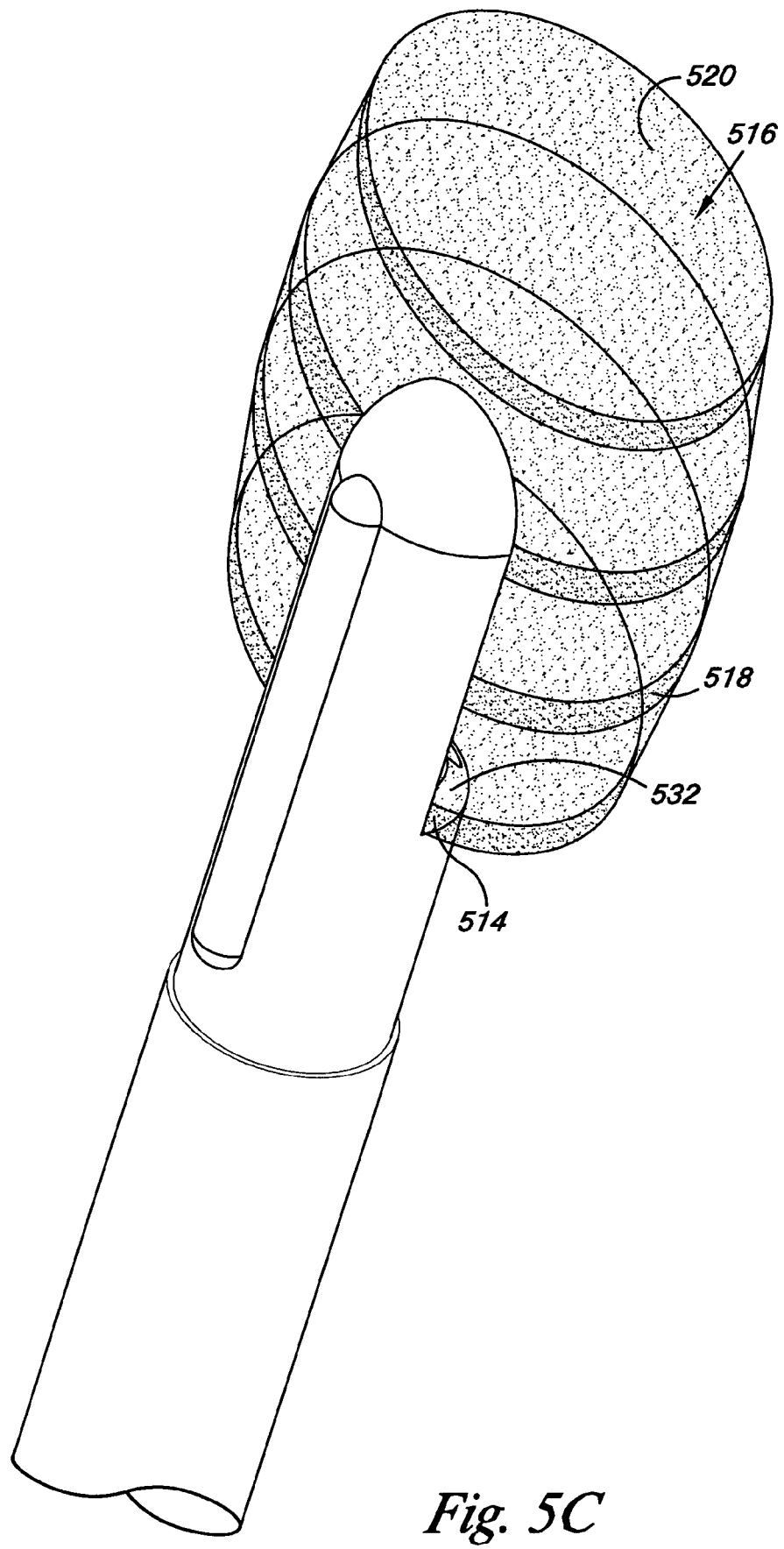
Figure 5D:
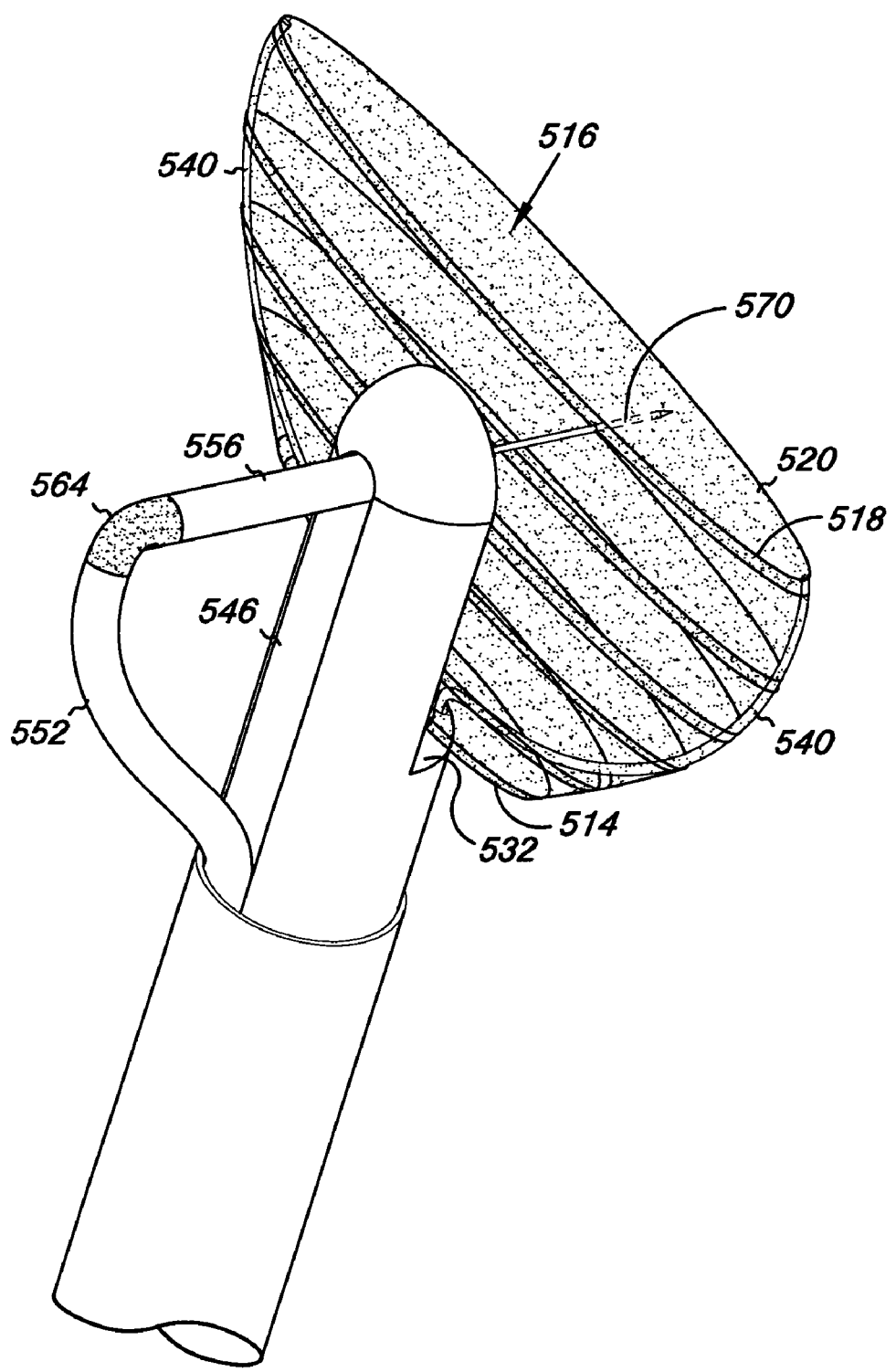
FIG. 5D provides an illustration of tightening the tissue defining the passage according to the teachings of the present invention.
Figure 5E:
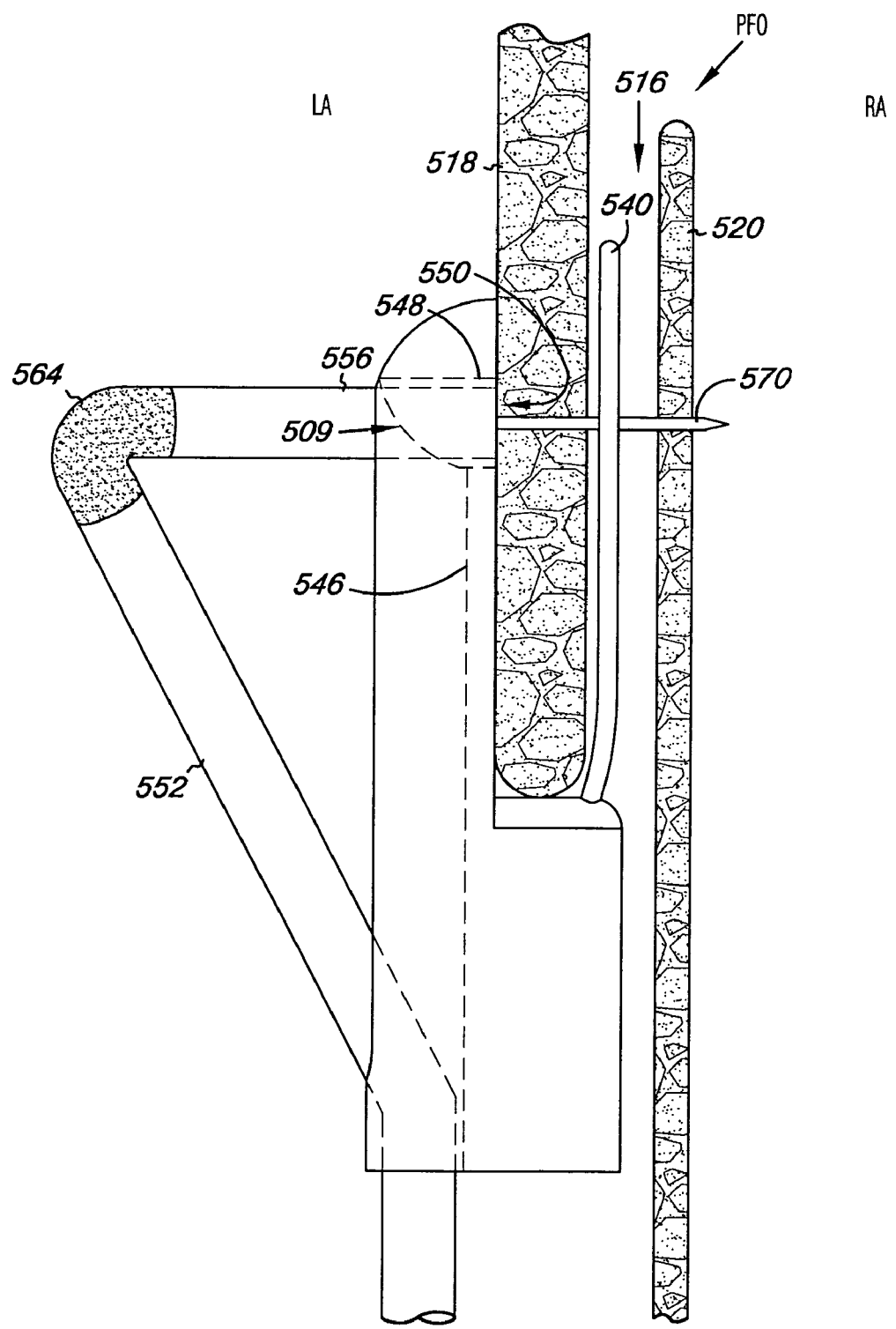
FIG. 5E provides an illustration of piercing the thick and thin tissue and of the passage according to the teachings of the present invention.

FIG. 5A provides an illustration for accessing the right atrium of the heart according to the present invention. FIGS. 5B and 5C provide illustrations for seating the positioning device on the limbus of the SS (thick tissue 518) according to the present invention. FIG. 5D provides an illustration of tightening the tissue defining the passage according to the present invention. FIG. 5E provides an illustration of piercing the thick and thin tissue of the passage so as to gain entry to the left atrium (LA) according to the present invention. Finally, FIG. 5F provides an illustration of an occluded or sealed passage according to the present invention.

As the reader will appreciate, tightening tissue of the passage, as shown in FIG. 5D, can be implemented prior to piercing the passage, as shown in FIGS. 5E and 5F. However, in some embodiments, the passage can be pierced and occluded without tightening the tissue of the passage.

The embodiments illustrated in FIGS. 5C and 5D show the passage 516 (i.e., the patent foramen ovale), among other things. For purposes of simplicity however, the PFO, illustrated in FIGS. 5C and 5D, includes dark bands on the upper portion, e.g., rightward portion, of the passage, which are labeled as 518. The dark bands are intended to illustrate that the upper, e.g., rightward, portion of the passage 516 is formed substantially of thick tissue 518 and the lower, leftward, portion of the passage 516 is formed of substantially thin tissue 520, as discussed herein.

In addition, the passage 516 illustrated in FIGS. 5C and 5D is intended to show, generally, a change in the shape of the passage 516. As discussed herein, the change in the shape of the passage 516 is the result of the arms 540 of the extension member 538 extending away from the ledge 532 so as to create the expansion force on the inner surfaces of the tissue, as discussed herein.

Referring now to FIG. 5A, the method for positioning the positioning device within the right atrium 502 includes introducing the catheter 576 into the venous system of the patient using a minimally invasive percutaneous, transluminal catheter based delivery system.

A unique aspect of the passage 516 is its location relative to the orifice of the inferior vena cava 512. Since the passage 516 is located above and to the left of the orifice of the inferior vena cava 512, the positioning device 522 can be deployed upon entering the right atrium 502 from the orifice of the inferior vena cava 512. For example, a guidewire can be positioned within the venous system and advanced to the right atrium 502 of a patient. In one embodiment, the right atrium 502 can be entered via the orifice of the inferior vena cava 512. The catheter 576, including the positioning device 522, as described herein, can be positioned over the guidewire and the catheter 576 advanced so as to position the distal end 582 of the catheter 576 at or adjacent the septal wall 506 of right atrium 502. Once positioned within the right atrium 502, the positioning device 522 can be deployed from the catheter 576.

In one embodiment, radiopaque markers on the catheter 576 and/or the positioning device 522 can be used to help positioning the positioning device 522 within the right atrium 502 and/or to seat the positioning device 522 on the limbus 514, as will be discussed herein. In addition, orientation and visualization of the positioning device 522 and the various components of the positioning device (e.g., elongate structure, piercing member, and extension member) may be accomplished through the use of any combination of echogenic, angioscopic, ultrasound, magnetic resonance imaging, and fluoroscopic visualization techniques.

Referring now to FIGS. 5A-5C, seating the positioning device 522 on the limbus 514 of the SS 518 can include positioning the elongate body 524 adjacent the limbus 514 of the SS 518. To do this, the deployed positioning device 522 can be positioned against the septal wall 506 and slid along the septal wall 506 of the right atrium toward the interatrial septum 508. Because the limbus 514 includes the pronounced anterosuperior margin of the fossa ovalis 510, the limbus 514 can catch the ledge 532 of the positioning device 522 as the positioning device 522 slides along the septal wall 506 to seat the positioning device on the limbus 514.

In various embodiments, seating the positioning device 522 on the limbus 514 can help to locate and properly position the various components of the positioning device 522. For example, seating the positioning device 522 on the limbus 514 of the SS 18 can include locating the extension member 538 of the positioning device 522 adjacent the passage 516, as shown in FIGS. 5B and 5C. Locating the extension member 538 adjacent the passage 516 helps to properly position the ledge opening 536 of the elongate body 524 such that the extension member 538 can be extended into the passage 516 without being obstructed by the limbus 514, as shown in FIGS. 5B and 5C.

In various embodiments, the method can include extending the extension member 538 into the passage 516. In various embodiments, extending the extension member into the passage 516 can include tightening tissue of the passage 516, as shown in FIG. 5D. In the native state, the tissues that form the passage can include elevations and/or depressions along the length of the passage and thus, the surfaces are generally not linear along the length of the passage. In various embodiments, tightening the tissue of the passage 516 can help to provide for a substantially linear surface of the tissues of the passage 516 relative to the surfaces that are not tightened. For example, once the extension member 538 has been extended from the elongate body 524, the arms 540 extend away from the ledge 532 of the elongate body 524. When the arms 540 extend away from the ledge 532, the arms 540 contact this tissue and create an expansion force, as discussed herein, against internal surfaces of the passage 516. In one embodiment, the internal surfaces can include the thin tissue 520 of the passage 516. In another embodiment, the internal surfaces can include thin tissue 520 and thick tissue 518 of the passage 516. The expansion force acting on the internal surfaces of the passage causes the tightening of the tissue of the passage so as to provide for substantially linear surfaces of the passage 516.

In various embodiments, tightening the tissue of the passage 516 can also include stretching the tissue of the passage 516 in different directions, such that the thin tissue 520 of the passage 516 is urged toward the thick tissue 518 of the passage 516, as shown in FIG. 5D. In one embodiment, urging the thin tissue 520 toward the thick tissue 518 of the passage 516 can provide for a reduced distance in which the piercing member 570 is extended from the elongate structure 552 to pierce both the thick and thin tissues 518 and 520 of the passage 516 as shown in FIGS. 5D and 5E. In addition, the extension member 538 can assure that the elongate body 524 of the positioning device 522 is correctly oriented with respect to the passage. This positioning mechanism assures correct alignment for the piercing member 570 as it pierces the thick and thin tissue 518 and 520 of the passage 516.

In various embodiments, piercing the tissue defining the passage 516 can include positioning the elongate structure 552 of the positioning device substantially perpendicular to the thick tissue 518 of the passage 516 as shown in FIGS. 5D and 5E. Positioning the elongate structure 552 can include pushing the elongate structure 552 away from the channel 546 of the elongate body 524 using the first deployment shaft 501, as discussed herein with respect to FIGS. 4A-4C. As the elongate structure 552 is pushed away from the channel 546, the flexible portion forms the predetermined bend and the distal end 556 of the elongate structure 552 rotates along the rotation point from the first position to the second position, as described herein with respect to FIGS. 2B-2D.

Positioning the elongate structure 552 substantially perpendicular to the thick and thin tissue 518 and 520 can help to properly position the piercing member 570 relative to the passage 516 such that the piercing member 570 can be pushed through the passage 516 at substantially a right angle relative to the thick and thin tissues 518 and 520 as shown in FIGS. 5D and 5E. In various embodiments, the rotation of the elongate structure 552 can rotate more than 90 degrees, and in other embodiments, the rotation of the elongate structure 552 can rotate less than 90 degrees.

In some embodiments, pushing the piercing member 570 through the thick tissue and the thin tissue 518 and 520 of passage 516 includes fastening the thick tissue and the thin tissue 518 and 520 to occlude the passage 516 of the fossa ovalis 510 as shown in FIG. 5F. As discussed herein, fastening the thick and thin tissue can involve traumatizing the thick and thin tissue by piercing the tissue so as to cause While the present invention has been shown and described in detail above, it will be clear to the person skilled in the art that changes and modifications may be made without departing from the scope of the invention. As such, that which is set forth in the foregoing description and accompanying drawings is offered by way of illustration only and not as a limitation. The actual scope of the invention is intended to be defined by the following claims, along with the full range of equivalents to which such claims are entitled.

In addition, one of ordinary skill in the art will appreciate upon reading and understanding this disclosure that other variations for the invention described herein can be included within the scope of the present invention. For example, the catheter can be coated with a non-thrombogenic biocompatible material, as are known or will be known.

In the foregoing Detailed Description, various features are grouped together in several embodiments for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. An apparatus, comprising:
a positioning device having an elongate body with a proximal end and a distal end, the elongate body includes a number of surfaces with one of the number of surfaces forming a wall having a wall opening, where the wall extends from the distal end toward the proximal end to a surface defining a ledge that extends away from the wall and includes a ledge opening, the elongate body includes a first lumen, a second lumen, and a third lumen, the first lumen extends toward the ledge, the second lumen extends toward the distal end of the elongate body, and the third lumen extends from the wall opening completely through the elongate body to a transverse opening to define the third lumen;
an extension member extendably positioned within the first lumen toward the distal end of the elongate body; and
an elongate structure extendably positioned within the second lumen toward the distal end of the positioning device, where the elongate structure passes to the third lumen.

2. The apparatus of claim 1, where the extension member includes at least one arm that extends away from the ledge when extended from the first lumen.

3. The apparatus of claim 2, where the at least one arm extends away from the ledge within a single plane.

4. The apparatus of claim 2, where the at least one arm extends away from the ledge in a number of different planes.

5. The apparatus of claim 1, where the extension member includes at least two arms that extend away from the ledge in opposite directions when extended from the first lumen.

6. The apparatus of claim 1, where the extension member includes at least two arms that extend away from the ledge in different directions and in different planes.

7. The apparatus of claim 1, where the elongate body includes a surface defining a channel extending longitudinally between the second lumen and the third lumen.

8. The apparatus of claim 7, where the elongate structure includes a flexible portion along which the elongate structure bends under a compression force to push the elongate structure away from the channel of the elongate body.

9. The apparatus of claim 1, where the elongate structure includes:
a lumen extending longitudinally between a proximal end and a distal end of the elongate structure; and
a piercing member releasably positioned within the lumen of the elongate structure proximal the distal end of the elongate structure.

10. The apparatus of claim 9, where the distal end of the elongate structure includes a rotation point along which the distal end of the elongate structure rotates under a compression force from a first position to a second position.

11. The apparatus of claim 10, where the rotation point includes a pivot along which the distal end of the elongate structure rotates under the compression force from the first position to the second position.

12. The apparatus of claim 1, including a piercing member slidably positioned within a lumen of the elongate structure.

13. The apparatus of claim 12, where the piercing member includes a therapeutic device.

14. The apparatus of claim 13, where the piercing member includes a diagnostic device.

15. A system, comprising:
a positioning device including:
an elongate body having a proximal end and a distal end, the elongate body includes a number of surfaces with one of the number of surfaces forming a wall having a wall opening, where the wall extends from the distal end toward the proximal end to a surface defining a ledge that extends away from the wall and includes a ledge opening, the elongate body includes a first lumen, a second lumen, and a third lumen, the first lumen extends toward the ledge, the second lumen extends toward the distal end of the elongate body, and the third lumen extends from the wall opening completely through the elongate body to a transverse opening to define the third lumen;

an extension member extendably positioned within the first lumen toward the ledge; and an elongate structure extendably positioned within the second lumen toward the distal end of the positioning device, where the elongate structure passes to the third lumen; and a catheter including a proximal end and a distal end, the positioning device located between the proximal end and the distal end of the catheter.

16. The system of claim 15, where the positioning device is slidably positioned within a lumen of the catheter toward the distal end of the catheter to deploy the positioning device from the distal end of the catheter.

17. The system of claim 16, where the first lumen of the elongate body includes a first deployment shaft therein and adjacent the proximal end of the extension member, the first deployment shaft moves within the first lumen of the elongate body to extend the extension member from the first lumen of the elongate body.

18. The system of claim 16, where the second lumen of the elongate body includes a second deployment shaft therein and adjacent the proximal end of the elongate structure, the second deployment shaft moves within the second lumen of the elongate body to extend the elongate structure away from the elongate body.

19. The system of claim 16, including a third deployment shaft positioned within a lumen of the elongate structure and adjacent a releasably positioned piercing member, the third deployment shaft moves within the lumen of the elongate structure to extend the piercing member from the lumen of the elongate structure.

20. The system of claim 15, where the extension member is formed of a shape memory material.

21. The system of claim 15, including a sheath having a proximal end and a distal end, the positioning device coupled to the sheath at the distal end of the sheath, the sheath slidably positioned within a lumen of the catheter to deploy the positioning device from the distal end of the catheter.

22. The system of claim 21, where the sheath includes a first lumen having a first deployment shaft therein and adjacent the proximal end of the extension member, the first deployment shaft moves within the first lumen of the sheath and the first lumen of the elongate body to extend the extension member from the first lumen of the elongate body.

23. The system of claim 21, where the sheath includes a second lumen having a second deployment shaft positioned therein and adjacent the proximal end of the elongate structure, the second deployment shaft moves within the second lumen of the sheath and the second lumen of the elongate body to extend the extension member away from the channel of the elongate body via the channel.

24. The system of claim 21, where the sheath includes a third lumen having a third deployment shaft positioned therein and adjacent the releasably positioned piercing member, the third deployment shaft moves within the third lumen of the sheath and the lumen of the elongate structure to extend and release the piercing member from the lumen of the elongate structure.

25. The system of claim 15, where the elongate structure includes:

a lumen extending longitudinally from a proximal end toward a distal end of the elongate structure; and a piercing member releasably positioned within the lumen of the elongate structure proximal the distal end of the elongate structure.

26. A method, comprising:

forming a positioning device that includes:

an elongate body having a proximal end and a distal end, the elongate body includes a number of surfaces with one of the number of surfaces forming a wall having a wall opening, where the wall extends from the distal end toward the proximal end to a surface defining a ledge that extends away from the wall and includes a ledge opening, the elongate body includes a first lumen, a second lumen, and a third lumen, the first lumen extends toward the ledge, the second lumen extends toward the distal end of the elongate body, and the third lumen extends from the wall opening completely through the elongate body to a transverse opening to define the third lumen;

an extension member extendably positioned within the first lumen toward the ledge; and an elongate structure extendably positioned within the second lumen toward the distal end of the positioning device, where the elongate structure passes to the third lumen; and slidably coupling the positioning device within a lumen of a catheter between a proximal and a distal end of the catheter.

27. The method of claim 26, including:

coupling the positioning device to a sheath; and slidably coupling the sheath within the lumen of the catheter toward the distal end of the catheter.

28. The method of claim 26, where forming the positioning device includes:

forming a lumen within the elongate structure, the lumen of the elongate structure extending longitudinally from a proximal end of the elongate structure toward a distal end of the elongate structure; and forming a piercing member releasably positioned within the lumen of the elongate structure proximal the distal end of the elongate structure.

* * * * *